(12) United States Patent
Bhowmick et al.

(10) Patent No.: US 11,957,323 B2
(45) Date of Patent: Apr. 16, 2024

(54) MEDICAL DEVICE HANDLE ASSEMBLIES AND METHODS OF USING THE SAME

(71) Applicant: Boston Scientific Medical Device Limited, Galway (IE)

(72) Inventors: Nabarun Bhowmick, Kolkata (IN); Deepak Kumar Sharma, Muzaffarnafar (IN); Shrikant Vasant Raut, Mumbai (IN); Subodh Morey, Ponda (IN); Charudatta Chandrakant Aradhye, Solapur (IN); James J. Scutti, Norwell, MA (US)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 217 days.

(21) Appl. No.: 17/179,099

(22) Filed: Feb. 18, 2021

(65) Prior Publication Data

US 2021/0251621 A1 Aug. 19, 2021

Related U.S. Application Data

(60) Provisional application No. 62/978,093, filed on Feb. 18, 2020.

(51) Int. Cl.
*A61B 17/00* (2006.01)
*A61M 25/01* (2006.01)

(52) U.S. Cl.
CPC .......... *A61B 17/00234* (2013.01); *A61B 2017/00323* (2013.01); *A61B 2017/00367* (2013.01); *A61M 25/0136* (2013.01)

(58) Field of Classification Search
CPC .... A61B 17/00234; A61B 2017/00323; A61B 2017/00367; A61M 25/0136
USPC .............................................................. 606/1
See application file for complete search history.

(56) References Cited

U.S. PATENT DOCUMENTS

2017/0105746 A1* 4/2017 O'Keefe .......... A61B 17/00234

* cited by examiner

*Primary Examiner* — Aaron F Roane
(74) *Attorney, Agent, or Firm* — Bookoff McAndrews, PLLC (57) ABSTRACT

A medical device that includes a handle including a plurality of actuators. The handle defines a longitudinal axis extending through a distal end of the handle. The device includes a shaft extending from the handle and an end effector at a distal end of the shaft. A first actuator of the plurality of actuators is configured to actuate the end effector in response to translation of the first actuator relative to the handle along an axis parallel to the longitudinal axis. A second actuator of the plurality of actuators is configured to deflect the end effector relative to the shaft in response to pivoting the second actuator about an axis transverse to the longitudinal axis. A third actuator of the plurality of actuators is configured to rotate the end effector relative to the shaft in response to rotation of the third actuator relative to the handle about the longitudinal axis.

15 Claims, 7 Drawing Sheets

MEDICAL DEVICE HANDLE ASSEMBLIES AND METHODS OF USING THE SAME

CROSS-REFERENCE TO RELATED APPLICATIONS

This application claims the benefit of priority from U.S. Provisional Application No. 62/978,093, filed Feb. 18, 2020, which is incorporated by reference herein in its entirety.

TECHNICAL FIELD

Various aspects of the disclosure relate generally to medical systems, devices, and related methods. More specifically, at least certain examples of the disclosure relate to systems, devices, and related methods for positioning and/or controlling one or more medical devices within a subject during a procedure via a handle assembly, among other aspects.

BACKGROUND

Technological developments have given users of medical systems, devices, and methods, the ability to conduct increasingly complex procedures on subjects. One challenge in the field of minimally invasive surgeries such as endoscopy, laparoscopy, and thoracoscopy, among other surgical procedures, is associated with providing control of medical devices during a procedure. Placement of such medical devices within a subject (e.g., a patient) may be difficult. Additionally, actuating various medical systems that control a placement of such medical devices may be counterintuitive or complex to understand. The limitations on medical devices that facilitate access of other devices into a patient for placement may prolong the procedure, limit its effectiveness, and/or cause injury to the patient due to device failure or breakage. There is a need for devices and methods that address one or more of these difficulties or other related problems

SUMMARY

Aspects of the disclosure relate to, among other things, systems, devices, and methods for accessing a target treatment site with a medical apparatus having intuitive handle assemblies that facilitate positioning of the apparatus, among other aspects. Each of the aspects disclosed herein may include one or more of the features described in connection with any of the other disclosed aspects.

According to an example, a medical device includes a handle including a plurality of actuators, wherein the handle defines a central longitudinal axis extending through a distal end of the handle. The medical device includes a shaft extending from the handle and an end effector at a distal end of the shaft. A first actuator of the plurality of actuators is configured to actuate the end effector in response to translation of the first actuator relative to the handle along an axis parallel to the central longitudinal axis. A second actuator of the plurality of actuators is configured to deflect the end effector relative to the shaft in response to pivoting the second actuator about an axis transverse to the central longitudinal axis. A third actuator of the plurality of actuators is configured to rotate the end effector relative to the shaft in response to rotation of the third actuator relative to the handle about the central longitudinal axis.

Any of the medical devices described herein may have any of the following features. The first actuator of the plurality of actuators includes a trigger positioned along a bottom wall of the handle. The trigger is configured to translate along the bottom wall of the handle along the axis parallel to the central longitudinal axis of the handle. Further including an actuation wire coupled to and extending between the trigger and the end effector. At least a portion of the trigger is movably received within an inner slot of the handle and is coupled to the actuation wire. Actuating the trigger moves the trigger along the inner slot and the actuation wire along the shaft to actuate the end effector. The second actuator of the plurality of actuators includes a rocker with a protrusion positioned along a top wall of the handle. Further including a pair of drive wires coupled to and extending between the rocker and the distal end of the shaft. Actuating the rocker moves at least one of the pair of drive wires along the shaft to deflect the distal end of the shaft. The third actuator of the plurality of actuators includes a roller positioned along a sidewall of the handle. The handle includes one or more walls defining an exterior of the handle, wherein each of the first actuator, the second actuator, and the third actuator are positioned along different walls of the one or more walls of the handle. Further including an actuation wire coupled to and extending between the roller and the end effector, wherein actuating the roller rotates the actuation wire and the end effector relative to the shaft. The handle includes one or more walls defining an exterior of the handle, wherein the first actuator is positioned along a top wall of the handle, and the second actuator and the third actuator are positioned along a first sidewall of the handle. The second actuator extends at least partially over the top wall of the handle.

According to another example, a medical device includes a handle including an actuation wire and a drive wire, a shaft extending from the handle, and an end effector at a distal end of the shaft. The handle is configured to actuate the end effector in response to the actuation wire translating relative to and independent of the drive wire. The handle is configured to deflect the end effector relative to the shaft in response to the drive wire translating relative to and independent of the actuation wire. The handle is configured to rotate the end effector relative to the shaft in response to the actuation wire rotating relative to and independent of the drive wire.

Any of the medical devices described herein may have any of the following features. The handle includes a first actuator configured to actuate the end effector along a first plane, a second actuator configured to deflect the end effector along a second plane that is transverse to the first plane, and a third actuator configured to rotate the end effector and adjust the first plane relative to the second plane. The handle is configured to deflect the end effector in a downward direction relative to the shaft in response to a distal translation of the drive wire relative to the actuation wire. The handle is configured to deflect the end effector in an upward direction relative to the shaft in response to a proximal translation of the drive wire relative to the actuation wire. The handle includes an actuator that is configured to translate the actuation wire relative to the drive wire. The actuator transitions the end effector to an open configuration when translating the actuation wire in a first longitudinal direction, and transitions the end effector to a closed configuration when translating actuation wire in a second longitudinal direction that is opposite of the first longitudinal direction. The handle includes an actuator that is configured to translate the drive wire relative to the actuation wire. The actuator deflects the end effector upward relative to the shaft when translating the actuation wire in a first longitudinal direction, and deflects the end effector downward when translating actuation wire in a second longitudinal direction that is opposite of the first longitudinal direction.

According to another example, a medical device includes a shaft including a distal end and a proximal end, an end effector at the distal end of the shaft, and a handle at the proximal end of the shaft. The handle includes a first actuator that is movable in a first direction relative to the handle, wherein the first actuator is configured to actuate the end effector in response to moving the first actuator in the first direction. The handle includes a second actuator that is movable in a second direction relative to the handle, wherein the second actuator is configured to deflect the end effector relative to the shaft in response to moving the second actuator in the second direction. The handle includes a third actuator that is movable in a third direction relative to the handle, wherein the third actuator is configured to rotate the end effector relative to the shaft in response to moving the third actuator in the third direction. The first direction is parallel to a longitudinal axis of the handle, and the third direction is about the longitudinal axis of the handle.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Examples of the disclosure include systems, devices, and methods for controlling multiple components of a medical device at a target site within the body, where the components generally require manipulation to access a target site, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject (e.g., patient). As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to facilitate control and positioning of an end effector (tools/devices) of a medical device at a target treatment site by providing one or more mechanisms and/or assemblies for positioning said tools/devices at the target treatment site. Some examples combine a handle assembly on a medical device for selective control and/or manipulation of components of the medical device, such as, for example, an end effector. The medical device may include a plurality of actuators along the handle assembly that are independently movable relative to one another for controlling a position and/or orientation of the end effector. The handle assembly is configured such that actuation of the plurality of actuators of the handle assembly may provide a respective rotation, actuation, and/or deflection of the end effector relative to the handle assembly.

Examples of the disclosure may relate to devices and methods for performing various medical procedures and/or treating portions of the large intestine (colon), small intestine, cecum, esophagus, any other portion of the gastrointestinal tract, and/or any other suitable subject anatomy (collectively referred to herein as a "target treatment site"). The device and related methods may be used laparoscopically or endoscopically, or in any other open or minimally invasive procedure, including thoracoscopic and ENT procedures. Reference will now be made in detail to examples of the present disclosure described above and illustrated in the accompanying drawings. Wherever possible, the same reference numbers will be used throughout the drawings to refer to the same or like parts.

Figure 1:
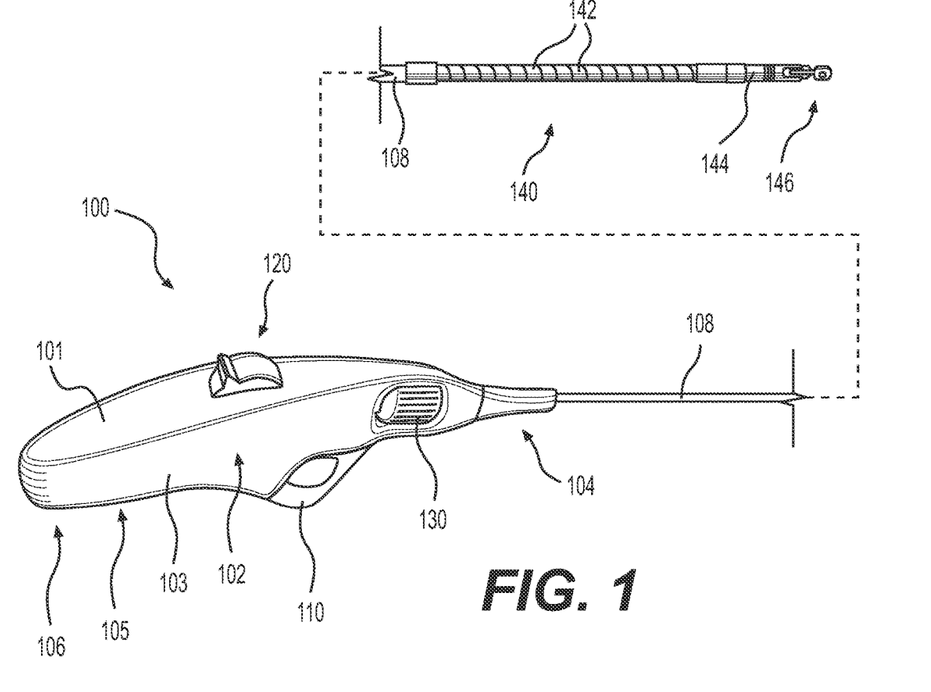
FIG. 1 is a perspective view of an exemplary medical device having a handle assembly and an end effector, according to aspects of this disclosure.

FIG. 1 shows a schematic depiction of an exemplary medical device 100 in accordance with an example of this disclosure. The medical device 100 may include a handle assembly 102 having a top wall 101, a pair of sidewalls 103, and a bottom wall 105. In the example, the top wall 101, the sidewalls 103, and the bottom wall 105 of the handle assembly 102 extend between a distal end 104 and a proximal end 106 that define a longitudinal length of the handle assembly 102. At least a portion of the longitudinal length of the handle assembly 102 (e.g., a distal portion proximate to the distal end 104), as defined by the top wall 101, the sidewalls 103, and the bottom wall 105, may define a central longitudinal axis 10 (FIG. 2) of the handle assembly 102. In other embodiments, the handle assembly 102 may be defined by additional, fewer, and/or different walls than those shown and described herein, including, for example, a pair of curved sidewalls 103 that are coupled to one another. As described in further detail below, the handle assembly 102 may include one or more bends and/or angles formed along one or more of the top wall 101, the sidewalls 103, and the bottom wall 105 such that at least a portion of the longitudinal length of the handle assembly 102 (e.g., a proximal portion proximate to the proximal end 106) may be transverse to the central longitudinal axis 10.

In this instance, with at least a portion of the longitudinal length of the handle assembly 102 being transverse to the central longitudinal axis 10 of the handle assembly 102, the top wall 101, the sidewalls 103, and the bottom wall 105 of the handle assembly 102 may be sized, shaped, and configured such that a hand of a user of the medical device 100 may form an ulnar deviation relative to a forearm of the user when manually grasping the handle assembly 102. In other words, the handle assembly 102 includes a configuration with the top wall 101, the sidewalls 103, and the bottom wall 105 that positions a hand of a user of the medical device 100 at an angle relative to a forearm of the user when the handle assembly 102 is grasped by the hand of the user.

The medical device 100 may further include a shaft 108 extending distally from the distal end 104 of the handle assembly 102, and an articulation joint 140 extending distally from a distal end of the shaft 108. The shaft 108 of the medical device 100 may be flexibly deformable such that an orientation and/or a configuration of the shaft 108 may be adjustable. The shaft 108 may define a longitudinal axis extending between a proximal end of the shaft 108, located adjacent to the handle assembly 102, and a distal end of the shaft 108 located adjacent to the articulation joint 140 of the medical device 100. In the example, the shaft 108 may be rotatably fixed relative to the handle assembly 102 and secured to, and/or coupled with, the articulation joint 140. Accordingly, and as described in further detail herein, the shaft 108 of the medical device 100 is configured to move (e.g., rotate) the articulation joint 140 in response to rotation of the handle assembly 102.

Still referring to FIG. 1, the medical device 100 may include one or more actuators 110, 120, 130 disposed along one or more exterior surfaces and/or walls of the handle assembly 102. In the example, the medical device 100 includes a first (actuation) actuator 110 positioned along the bottom wall 105 of the handle assembly 102, a second (articulation) actuator 120 positioned along the top wall 101 of the handle assembly 102, and a third (rotation) actuator 130 positioned along one or more of the sidewalls 103 of the handle assembly 102. The first (actuation) actuator 110 of the medical device 100 is configured to translate relative to the handle assembly 102, such as, for example, in one or more directions (e.g., distally, proximally, etc.) parallel to the central longitudinal axis 10 of the handle assembly 102. In the example, the first (actuation) actuator 110 is sized and shaped in the form of a trigger.

The second (articulation) actuator 120 of the medical device 100 may be configured to pivot relative to the handle assembly 102, such as, for example in one or more directions (e.g., distally, proximally, etc.) parallel to the central longitudinal axis 10 of the handle assembly 102. In other words, the second (articulation) actuator 120 pivots about an axis (not shown) that is transverse (e.g., perpendicular) to the central longitudinal axis 10 of the handle assembly 102. In the example, the second (articulation) actuator 120 may be a button/actuator that is sized and shaped in the form of a rocker, switch, a rotary slider, a knob and/or the like. For example, as shown in FIG. 1, the second (articulation) actuator 120 may comprise a rocker having a base wheel and one or more projections for secure placement of a user's thumb or fingers for actuation thereof. The second (articulation) actuator 120 may extend outwardly from the top wall 101 of the handle assembly 102 to facilitate access to the second (articulation) actuator 120 by a user of the medical device 100. For example, the rocker of the second (articulation) actuator 120 may be at least partially rotatable and/or pivotable about an axis that is relatively transverse to the central longitudinal axis 10 (FIG. 2) of the handle assembly 102. In the example, the projections of the second (articulation) actuator 120 may be movable in one or more directions that is at least relatively parallel to the central longitudinal axis 10.

Still referring to FIG. 1, the third (rotation) actuator 130 may be configured to rotate (e.g., clockwise, counter-clockwise, etc.) relative to the handle assembly 102, such as, for example, about an axis (not shown) that is collinear or parallel to the central longitudinal axis 10 of the handle assembly 102. In the example, the third (rotation) actuator 130 is a button/actuator that is sized and shaped in the form of a roller, a drum, and/or the like. In some examples, the third (rotation) actuator 130 may extend laterally outward from at least one (or both) of the sidewalls 103 of the handle assembly 102 to facilitate access to the third (rotation) actuator 130 by a user of the medical device 100. In other examples, the third (rotation) actuator 130 may be fully disposed within the handle assembly 102 and one or more of the sidewalls 103 of the handle assembly 102 may include a recess and/or opening that is sized, shaped, and aligned with a location of the third (rotation) actuator 130. In this instance, the opening on the handle assembly 102 may be operable to facilitate access to the third (rotation) actuator 130 to a user of the medical device 100.

It should be appreciated that additional and/or fewer actuators 110, 120, 130 may be included on various other walls 101, 103, 105 (and/or surfaces) of the handle assembly 102 without departing from the scope of this disclosure. It should further be understood that, in other examples, the actuators 110, 120, 130 may have various other configurations than those shown and described herein (see FIGS. 6-7). Additionally, the handle assembly 102 may include one or more actuators 110, 120, 130 that are any combination of an actuation, articulation, and/or rotation actuator. As described in further detail herein, the actuators 110, 120, 130 are configured and operable to actuate one or more components of the medical device 100, such as, for example, an articulation joint 140 and/or an end effector 146.

In embodiments, a position of the actuators 110, 120, 130 on the handle assembly 102 may be provided in an ergonomic manner such that the actuators 110, 120, 130 may be operable by a single hand of a user of the medical device 100. For example, the actuators 110, 120, 130 may be positioned such that a first finger (e.g., an index finger) may operate the first (actuation) actuator 110, a second finger (e.g., a thumb) may operate the second (articulation) actuator 120, and a third finger and/or at least one of the first or second fingers may operate the third (rotation) actuator 130. In this instance, the medical device 100 may be operable to provide control of the handle assembly 102 with a single hand, thereby facilitating control of a second device (e.g., an endoscope, medical instrument, etc.) with another hand during a medical procedure.

Still referring to FIG. 1, the articulation joint 140 of the medical device 100 may include a plurality of articulation links 142 and a clevis 144. The plurality of articulation links 142 may be sequentially aligned with one another and at least partially define a longitudinal length of the articulation joint 140. In the example, the plurality of articulation links 142 are movably coupled to one another such that each of the plurality of articulation links 142 are configured to move (e.g., bend, pivot, deflect) relative to one another. In an unactuated state, a longitudinal length of the articulation joint 140, defined by the plurality of articulation links 142, may be substantially parallel to a longitudinal axis of the shaft 108. As described above, a distal end of the shaft 108 may be positioned adjacent to and/or secured at a proximal end of the articulation joint 140, such as, for example, a first (i.e., proximalmost) articulation link 142 of the plurality of articulation links 142.

The clevis 144 may extend distally from and/or be coupled to a distal end of the articulation joint 140, such as, for example, a last (i.e., distalmost) articulation link 142 of the plurality of articulation links 142. The end effector 146 of the medical device 100 extends distally from a distal end of the clevis 144. It should be appreciated that the end effector 146 of the medical device 100 may include various suitable components, including, but not limited to, one or more clamps, shears, forceps, suturing devices, lighting devices, imaging systems, grasper assemblies, and various other suitable tools and/or devices. Accordingly, the end effector 146 shown and described herein is merely provided for exemplary purposes and may include various other configurations without departing from the scope of this disclosure. With the end effector 146 and the clevis 144 of the medical device 100 positioned relatively distal of the articulation joint 140, it should be understood that movement of the plurality of articulation links 142 may provide movement of the end effector 140 and the clevis 144 relative to at least a distal end of the shaft 108.

Figure 2:
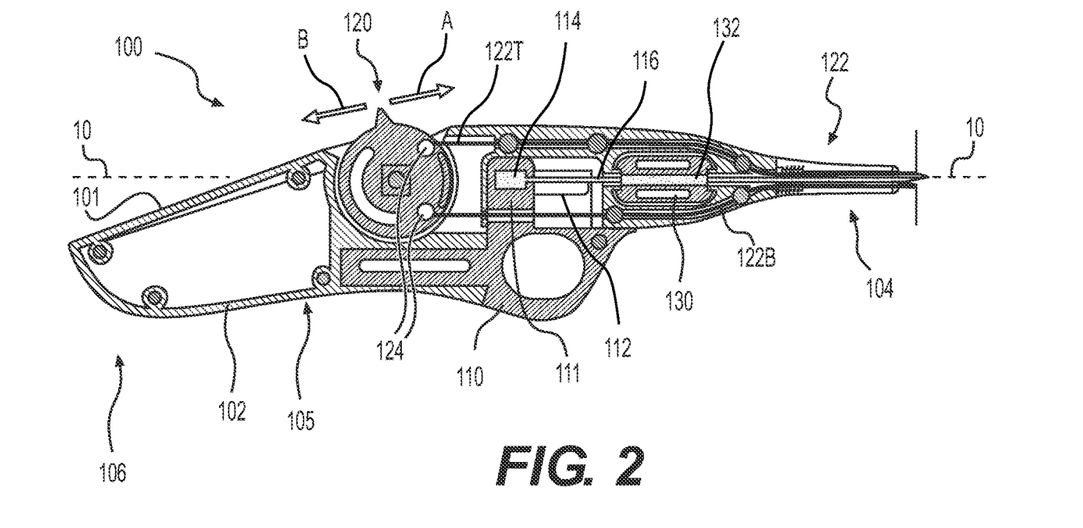
FIG. 2 is a cross-sectional side view of the handle assembly of the medical device of FIG. 1, including an actuator, according to aspects of this disclosure.

Referring now to FIG. 2, the handle assembly 102 of the medical device 100 further includes a slot 112 formed within a cavity of the handle assembly 102. Further, the first (actuation) actuator 110 may include a slider 111 that is sized, shaped, and configured to be slidably received within the slot 112 of the handle assembly 102. The slider 111 may be configured and operable to translate relative to the handle assembly 102 along the slot 112 in response to translation of at least the portion of the first (actuation) actuator 110. As described in greater detail herein, the slider 111 of the first (actuation) actuator 110 may include a cavity disposed therein that is sized and shaped to receive one or more components of the medical device 100 therein, such as, for example, at least a portion of an actuation wire 116. The handle assembly 102 of the medical device 100 further includes a rotation joint 132 disposed along at least a portion of the third (rotation) actuator 130. Accordingly, the rotation joint 132 is configured and operable to rotate relative to the handle assembly 102 in response to rotation of the third (rotation) actuator 130 within the handle assembly 102. As described in further detail herein, the rotation joint 132 is rotatably fixed relative to the third (rotation) actuator 130 and longitudinally translatable relative to the third (rotation) actuator 130.

Still referring to FIG. 2, the third (rotation) actuator 130 may include a cavity that is sized and shaped in accordance with a configuration of the rotation joint 132 such that the rotation joint 132 may be received within the cavity of the third (rotation) actuator 130. By way of illustrative example, the rotation joint 132 may include a rectangular (and/or cuboidal) shape and a cavity of the third (rotation) actuator 130 may be likewise rectangularly (and/or cuboidal) shaped, such that the corresponding configurations of the rotation joint 132 and the cavity of the third (rotation) actuator 130 may key and/or rotatably fix the rotation joint 132 to the third (rotation) actuator 130, while permitting axial translation therebetween.

In this instance, the rotation joint 132 may be configured to translate through, along, and/or relative to the cavity of the third (rotation) actuator 130 and be inhibited from rotating independent of the third (rotation) actuator 130. For example, due to the interaction between the edges, points, and/or contacts planes of the rotation joint 132 with one or more surfaces of the cavity of the third (rotation) actuator 130, rotation of third (rotation) actuator 130 may result in likewise rotation of the rotation joint 132. Additionally, due to the corresponding configurations of the rotation joint 132 and the cavity of the third (rotation) actuator 130, axial advancement of the rotation joint 132 (e.g., as caused by actuation of first (actuation) actuator 110) will not result in likewise advancement of third (rotation) actuator 130. As described in detail herein, the rotation joint 132 may be monolithically formed with, and/or fixedly coupled to (e.g., immovable relative to), one or more components of the medical device 100, such as, for example, an actuation wire 116.

The medical device 100 may further include an actuation wire 116 and one or more drive wires 122 (e.g., top drive wire 122T, bottom drive wire 122B) disposed within the handle assembly 102. In the example, the actuation wire 116 is secured and/or coupled to the slider 111 at a proximal end of the actuation wire 116. For example, the actuation wire 116 includes a hub 114 at a proximal end of the actuation wire 116 that is sized and shaped in accordance with the cavity formed in the slider 111 of the first (actuation) actuator 110, such that the hub 114 is received within the cavity of the slider 111. It should be appreciated that the hub 114 may comprise an enlargement and/or protrusion positioned at a proximal end of the actuation wire 116. In some examples, the hub 114 of the actuation wire 116 may be monolithically formed with, and/or fixedly coupled to (e.g., immovable relative to), the actuation wire 116. Additionally, the hub 114 may be sized and shaped to be movable (e.g., rotatable) relative to the cavity of the slider 111 in which the hub 114 is disposed.

In other words, the slider 111 of the first (actuation) actuator 110 may include a cavity that is sized and shaped in accordance with a configuration of the hub 114 such that the hub 114 may be received within, and movable relative to, the cavity of the slider 111 of the first (actuation) actuator 110. By way of illustrative example, the hub 114 may include a cylindrical shape and a cavity of the slider 111 may be cylindrically shaped such that movement (e.g., rotation) of the hub 114 relative to the cavity of the slider 111 is permitted.

The actuation wire 116 has a longitudinal length that extends through the handle assembly 102 and the shaft 108. In the example, the actuation wire 116 extends through at least a portion of the first (actuation) actuator 110 and the third (rotation) actuator 130. For example, the hub 114 of the actuation wire 116 is received in the slider 111 of the first (actuation) actuator 110 and through the rotation joint 132, which is disposed within the third (rotation) actuator 130. In this instance, the hub 114 is configured and operable to move (e.g., translate) the actuation wire 116 relative to the handle assembly 102 in response to, for example, translation of the first (actuation) actuator 110 and the slider 111 within the slot 112. Further, the rotation joint 132 is secured to and/or coupled with the actuation wire 116 such that the rotation joint 132 is configured and operable to move (e.g., rotate) the actuation wire 116 relative to the handle assembly 102 in response to, for example, rotation of the third (rotation) actuator 130 and the rotation joint 132.

Still referring to FIG. 2, with the hub 114 of the actuation wire 116 secured to and/or coupled with the slider 111, as described above, it should be understood that rotation of the rotation joint 132 may provide a simultaneous rotation of the hub 114 within the cavity of slider 111 of the first (actuation) actuator 110. Further, with at least a portion of the actuation wire 116 extending through and/or fixedly coupled to the rotation joint 132, as described above, it should be understood that translation of the slider 111, and the hub 114 disposed therein, may provide a simultaneous translation of the rotation joint 132 relative to the third (rotation) actuator 130. It should be appreciated that a longitudinal length of the rotation joint 132 is such that at least a portion of the rotation joint 132 may remain disposed within the third (rotation) actuator 130 during translation of the rotation joint 132 relative to the third (rotation) actuator 130. In this instance, rotation of the third (rotation) actuator 130 may provide rotation of the rotation joint 132 and the actuation wire 116 despite an extent of translation of the slider 111 relative to the slot 112.

Although not shown, it should be understood that the actuation wire 116 may extend through the shaft 108 of the medical device 100 and a second, distal end of the actuation wire 116 may be secured and/or coupled to the end effector 146 of the medical device 100. As described further herein, the actuation wire 116 is configured to actuate the end effector 146 of the medical device 100 in response to an actuation of the first (actuation) actuator 110. Additionally, the actuation wire 116 is further configured to rotate the end effector 146 relative to the shaft 108 and/or the articulation joint 140 in response to rotation of the third (rotation) actuator 130 relative to the handle assembly 102.

Still referring to FIG. 2, the handle assembly 102 includes a pair of drive wires 122 (e.g., top drive wire 122T, bottom drive wire 122B) secured and/or coupled to the second (articulation) actuator 120 within the handle assembly 102. In the example, a first, proximal end of each of the drive wires 122T, 122B is secured to the second (articulation) actuator 120 at respective connection points 124. The drive wires 122T, 122B have a longitudinal length that extend through the handle assembly 102. Although not shown, it should be understood that the drive wires 122T, 122B may extend through the shaft 108 of the medical device 100 and a second, distal end of each of the drive wires 122T, 122B may be secured and/or coupled to the articulation joint 140 of the medical device 100. For instance, a distal end of the drive wires 122T, 122B may be secured to a distalmost articulation link 142 of the plurality of articulation links 142, such as, for example, on opposing sides/portions of the distalmost articulation link 142. As described further herein, the pair of drive wires 122T, 122B are configured to articulate the articulation joint 140 of the medical device 100, such as the plurality of articulation links 142, in response to actuation of the second (articulation) actuator 120.

Figure 4A:
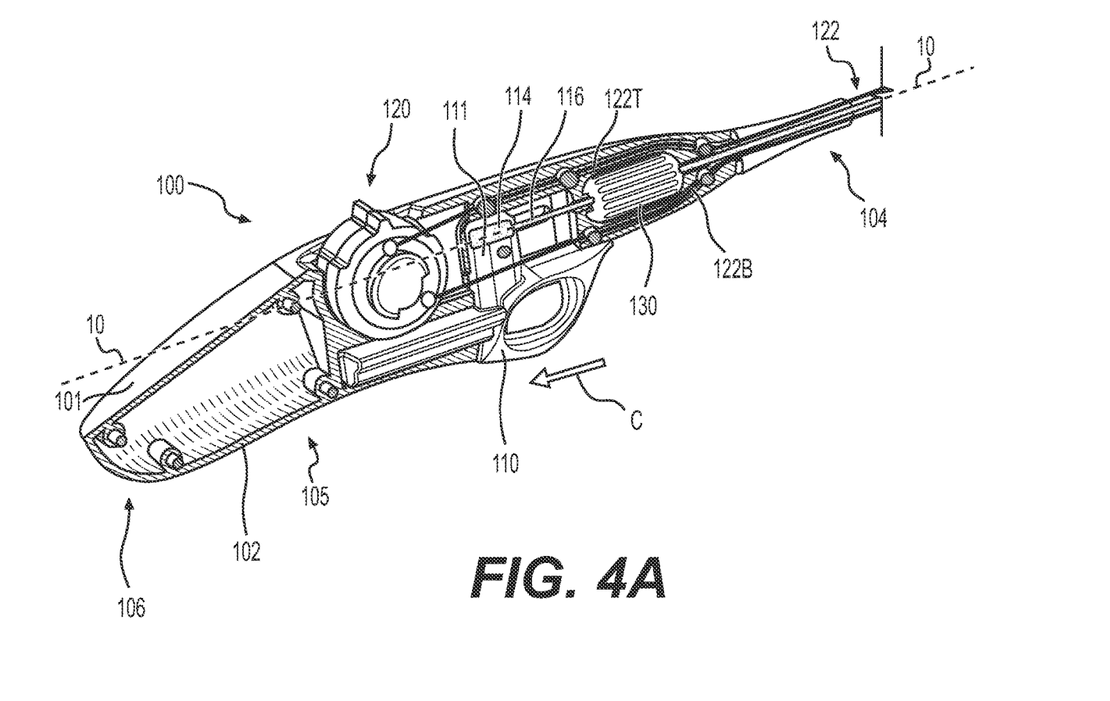
FIG. 4A is a cross-sectional side view of the handle assembly of the medical device of FIG. 1, including an actuator in a first actuated state, according to aspects of this disclosure.
Figure 4B:
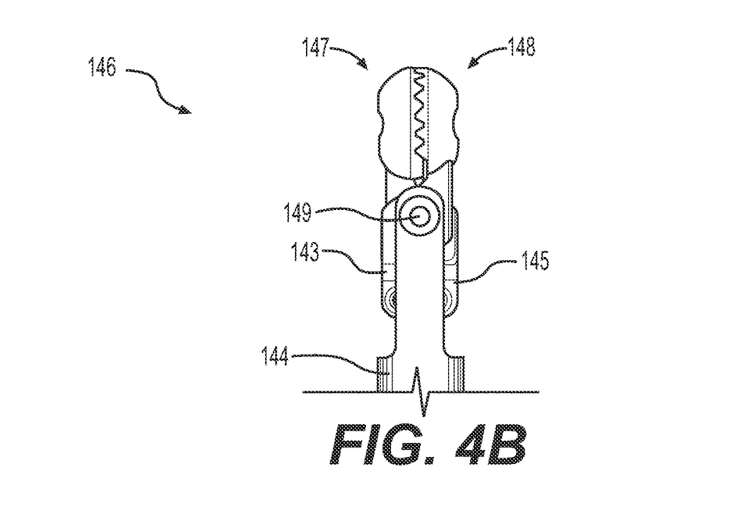
FIG. 4B is a partial side view of the end effector of the medical device of FIG. 1 in the first actuated state, according to aspects of this disclosure.
Figure 5A:
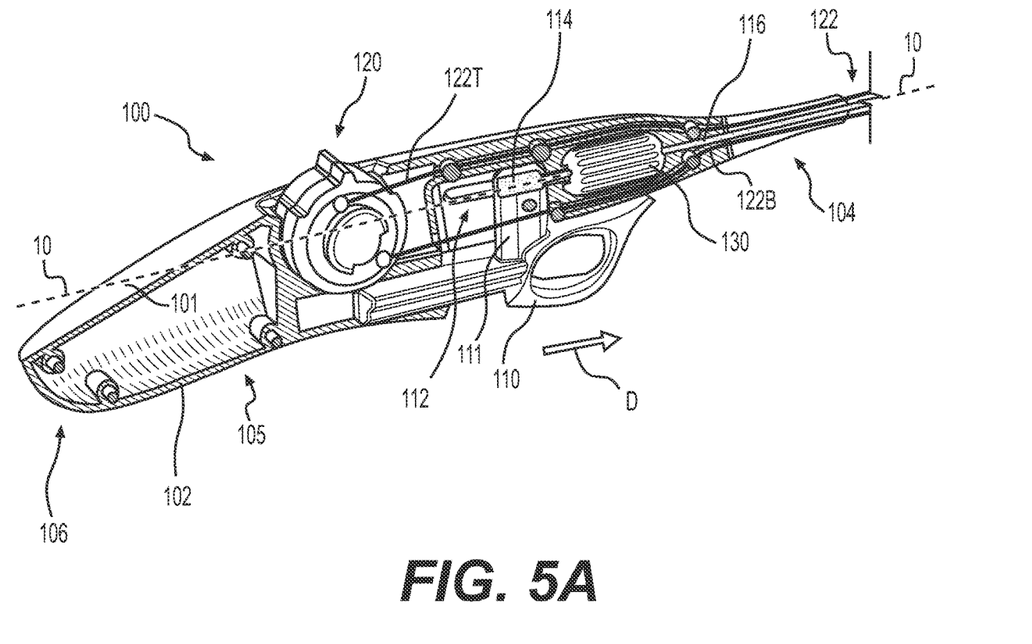
FIG. 5A is a cross-sectional side view of the handle assembly of the medical device of FIG. 1, with an actuator in a second actuated state, according to aspects of this disclosure.
Figure 5B:
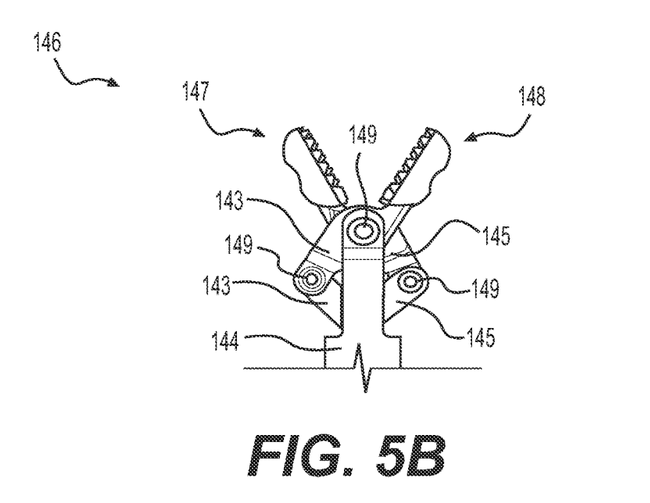
FIG. 5B is a partial side view of the end effector of the medical device of FIG. 1 in the second actuated position, according to aspects of this disclosure.

Referring now to FIGS. 4B and 5B, in some embodiments, the end effector 146 of the medical device 100 includes a plurality of first links 143, a plurality of second links 145, a first jaw 147, and a second jaw 148. At least one of the plurality of first links 143 (i.e., a proximalmost first link 143) is movably coupled to the clevis 144 and at least one of the plurality of second links 145 (i.e., a proximalmost second link 145) is movably coupled to the clevis 144. At least one of the plurality of first links 143 (i.e., a distalmost first link 143) is movably coupled to a proximal end of the second jaw 148 and at least one of the plurality of second links 145 (i.e., a distalmost second link 145) is movably coupled to a proximal end of the first jaw 147. In other examples, the first links 143 and the second links 145 may be arranged such that at least one of the plurality of first links 143 (e.g., a distalmost first link 143) is movably coupled to a proximal end of the first jaw 147, and at least one of the plurality of second links 145 (e.g., a distalmost second link 145) is movably coupled to a proximal end of the second jaw 148.

As best seen in FIG. 5B, each of the plurality of first links 143 and each of the plurality of second links 145 may include a pivot joint 149 at opposing, terminal ends of the links 143, 145, respectively. Accordingly, each of the plurality of first links 143 may be movably (e.g., rotatably) coupled to one another at opposing ends of the first links 143 via respective pivot joints 149. Each of the plurality of second links 145 may be movably (e.g., rotatably) coupled to one another at opposing ends of the second links 145 via respective pivot joints 149. Further, the distalmost first link 143 is movably coupled to the second jaw 148 via the pivot point 149, and the distalmost second link 145 is movably coupled to the first jaw 147 via the pivot point 149.

In the example, the end effector 146 includes a pair of first links 143 and a pair of second links 145. Accordingly, the proximalmost first link 143 is movably coupled to the distalmost first link 143 by engaging the respective pivot joints 149 of each first link 143 to one another. The proximalmost second link 145 is movably coupled to the distalmost second link 145 by engaging the respective pivot joints 149 of each second link 145 to one another. It should be understood that the end effector 146 may include additional and/or fewer links 143, 145 than those shown and described herein without departing from the scope of this disclosure. The proximalmost first link 143 and the proximalmost second link 145 are secured to and/or coupled with a distal end of the actuation wire 116 at the respective pivot joints 149 of each link 143, 145.

It should be appreciated that the actuation wire 116 is coupled to the proximalmost links 143, 145 within and/or through the clevis 144. As described in greater detail below, movement of the actuation wire 116 (e.g., translation) relative to the handle assembly 102 and/or the shaft 108 may provide movement of the plurality of links 143, 145 (including the proximalmost links 143, 145, the distalmost links 143, 145, and the like). With the plurality of links 143, 145 coupled to the jaws 147, 148 of the end effector 146, movement of the actuation wire 116 may further provide movement of the pair of jaws 147, 148 relative to the clevis 144 and/or to one another.

According to an exemplary method of using the medical device 100, the medical device 100 may be used to treat a target treatment site within a subject by positioning the end effector 146 adjacently thereto. The medical device 100 may be used for various suitable procedures, including, but not limited to, endoluminal surgical procedures such as endoscopic mucosal resection (EMR), endoscopic submucosal dissection (ESD), pre-oral endoscopic myotomy (POEM), and the like. It should be understood that the steps of the exemplary method described herein, and the sequence in which they are presented, are merely illustrative such that additional and/or fewer steps may be included without departing from the scope of this disclosure. It should further be appreciated that the exemplary method of utilizing the medical device 100 described and shown herein may be employed for various other procedures and used with various medical systems, devices, instruments, and/or assemblies, such as, for example, an endoscope (e.g., duodenoscope).

Referring back to FIGS. 1-2, the medical device 100 may be actuated by moving (e.g., rotating) the third (rotation) actuator 130 to rotate the end effector 146 relative to the articulation joint 140, the shaft 108, and/or the handle assembly 102. For example, the third (rotation) actuator 130 may be rotated in a clockwise and/or counter-clockwise direction relative to the central longitudinal axis 10 of the handle assembly 102. In this instance, with the actuation wire 116 disposed within the handle assembly 102 and secured to and/or coupled with the third (rotation) actuator 130 via the rotation joint 132, the actuation wire 116 is rotated when the third (rotation) actuator 130 rotates. Accordingly, rotation of the third (rotation) actuator 130 in a direction may provide a simultaneous rotation of the end effector 146 relative to and independent of the articulation joint 140, the shaft 108, and/or the handle assembly 102 as the end effector 146 is coupled to a distal end of the actuation wire 116. In other instances, the shaft 108 and/or the articulation joint 140 may be rotated with the end effector 146 of the medical device 100 in response to a rotation of the handle assembly 102 by a user of the medical device 100.

Further, the medical device 100 may be actuated by moving (e.g., pivoting) the second (articulation) actuator 120 to articulate the articulation joint 140. For example, the second (articulation) actuator 120 may be pivoted in a first (distal) direction A and/or a second (proximal) direction B relative to the handle assembly 102 of the medical device 100. In this instance, with the pair of drive wires 122 disposed within the handle assembly 102 and secured to the second (articulation) actuator 120 at the connection points 124, the drive wires 122 are actuated when the second (articulation) actuator 120 moves, thereby articulating the articulation joint 140. For example, movement of the second (articulation) actuator 120 in the first (distal) direction A may provide a proximal retraction (e.g., pulling) of at least one of the drive wires 122, and a simultaneous relaxation and/or distal extension of the other drive wire 122.

As described above, with each of the pair of drive wires 122T, 122B secured to opposing sides/portions of the distalmost articulation link 142 of the plurality of articulation links 142 (e.g., adjacent to the clevis 144), the articulation joint 140 is operable to articulate (e.g., bend, pivot, deflect, etc.) in a direction of the drive wire 122T, 122B that is retracted (i.e., pulled) proximally. In this instance, upon the second (articulation) actuator 120 being pivoted in the first (distal) direction A, the drive wire 122B positioned along a lower/bottom portion of the second (articulation) actuator 120 is tensioned and thereby pulled proximally relative to the opposing drive wire 122T positioned along an upper/top portion of the second (articulation) actuator 120. Accordingly, the top drive wire 122T is relaxed and/or extended distally relative to the bottom drive wire 122B.

Figure 3A:
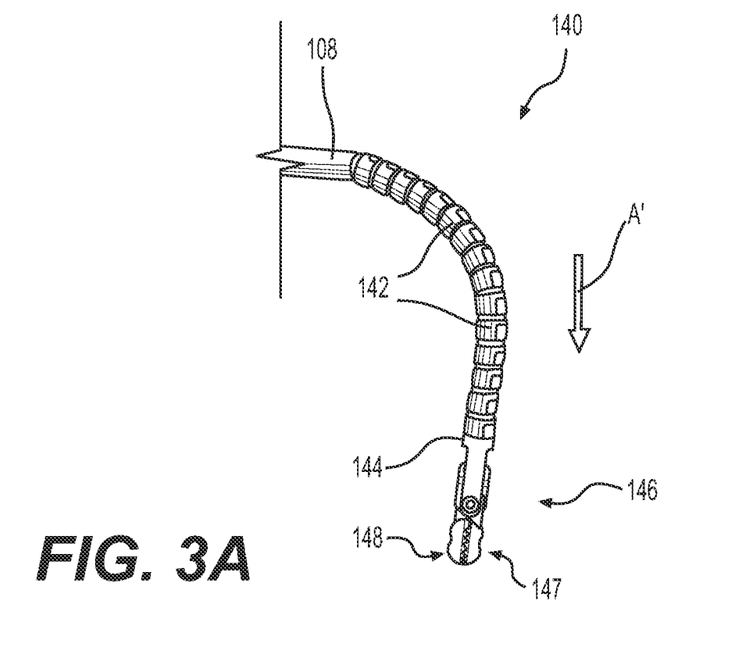
FIG. 3A is a partial perspective view of the end effector of the medical device of FIG. 1 in a first articulated position, according to aspects of this disclosure.

As seen in FIG. 3A, the plurality of articulation links 142 of the articulation joint 140 is articulated in the direction A' relative to the central longitudinal axis 10 of the handle assembly 102 and/or the shaft 108. As a result of pivoting the second (articulation) actuator 120 in the first (distal) direction A, the end effector 146 is moved in accordance with an articulation of the articulation joint 140 in a downward direction relative to the central longitudinal axis 10 of the handle assembly 102 and/or the shaft 108. Additionally and/or alternatively, the medical device 100 may be actuated by moving (e.g., pivoting) the second (articulation) actuator 120 in the second (proximal) direction B relative to the handle assembly 102 to articulate the articulation joint 140. In this instance, the drive wires 122T, 122B are actuated such that at least one of the drive wires 122T, 122B is retracted (i.e., pulled) proximally while the other drive wire 122T, 122B is relaxed and/or extended distally. As described above, the articulation joint 140 is operable to articulate (e.g., bend, pivot, deflect, etc.) in a direction of the drive wire 122T, 122B that is retracted (pulled) proximally. In this instance, the drive wire 122T, 122B positioned relative to the handle assembly 102 along an upper/top portion of the second (articulation) actuator 120 (e.g., the top drive wire 122T) is tensioned and thereby pulled proximally relative to the opposing drive wire 122T, 122B positioned along a lower/bottom portion of the second (articulation) actuator 120 (e.g., the bottom drive wire 122B).

Figure 3B:
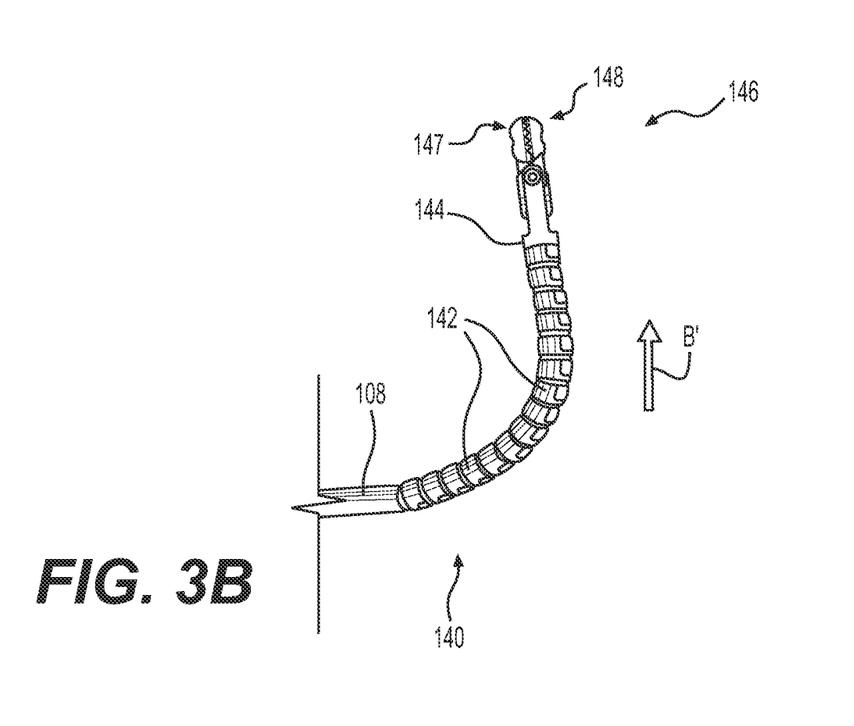
FIG. 3B is a partial perspective view of the end effector of the medical device of FIG. 1 in a second articulated position, according to aspects of this disclosure.

Accordingly, the bottom drive wire 122B is relaxed and/or extended distally relative to the top drive wire 122T. As seen in FIG. 3B, the plurality of articulation links 142 of the articulation joint 140 is articulated in the direction B' relative to the central longitudinal axis 10 of the handle assembly 102 and/or the shaft 108. As a result of pivoting the second (articulation) actuator 120 in the second (proximal) direction B, the end effector 146 is moved in accordance with an articulation of the articulation joint 140 in an upward direction relative to the central longitudinal axis 10 of the handle assembly 102 and/or the shaft 108. In other examples, the second (articulation) actuator 120 and/or the pair of drive wires 122T, 122B may be configured such that actuation of the second (articulation) actuator 120 may provide lateral (e.g., left/right) articulation (e.g., deflection) of the end effector 146 relative to the articulation joint 140 and/or the shaft 108 of the medical device 100.

Referring now to FIGS. 4A-4B, the medical device 100 may be further actuated by actuating the first (actuation) actuator 110 to actuate the end effector 146. For example, the first (actuation) actuator 110 may be moved (e.g., translated) in a first (proximal) direction C relative to the handle assembly 102. In this instance, the slider 111 of the first (actuation) actuator 110 received within the slot 112 may be moved to a proximal, terminal end of the slot 112. With the hub 114 of the actuation wire 116 secured to and/or coupled with the first (actuation) actuator 110 within the slider 111, the actuation wire 116 may simultaneously translate with the first (actuation) actuator 110 in the first (proximal) direction C relative to the handle assembly 102.

In this instance, the actuation wire 116 moves proximally and pulls the plurality of first links 143 and the plurality of second links 145 in the first (proximal) direction C. In response, the plurality of links 143, 145 may move (e.g., pivot) about the respective pivot points 149 and relative to one another to move the pair of jaws 147, 148 relative to one another to a closed configuration. In other words, a proximal retraction of the actuation wire 116 moves the plurality of links 143, 145 toward one another thereby closing the pair of jaws 147, 148 relative to each other.

Additionally and/or alternatively, referring now to FIGS. 5A-5B, the medical device 100 may be actuated by moving the first (actuation) actuator 110 in a second (distal) direction D relative to the handle assembly 102. In this instance, the slider 111 of the first (actuation) actuator 110 received within the slot 112 may be moved to a distal, terminal end of the slot 112. With the hub 114 of the actuation wire 116 secured to and/or coupled with the first (actuation) actuator 110 at the slider 111, the actuation wire 116 may simultaneously translate with the first (actuation) actuator 110 in the second (distal) direction D relative to the handle assembly 102.

In this instance, the actuation wire 116 may move distally and push the plurality of first links 143 and the plurality of second links 145 in the second (distal) direction D. In response, the plurality of links 143, 145 may move (e.g., pivot) about the respective pivot points 149 and relative to one another to move the pair of jaws 147, 148 outwardly relative to one another to an open configuration. In other words, a distal extension of the actuation wire 116 moves the plurality of links 143, 145 away from one another thereby permitting the pair of jaws 147, 148 to move outwardly (open) relative to each other.

Figure 6:
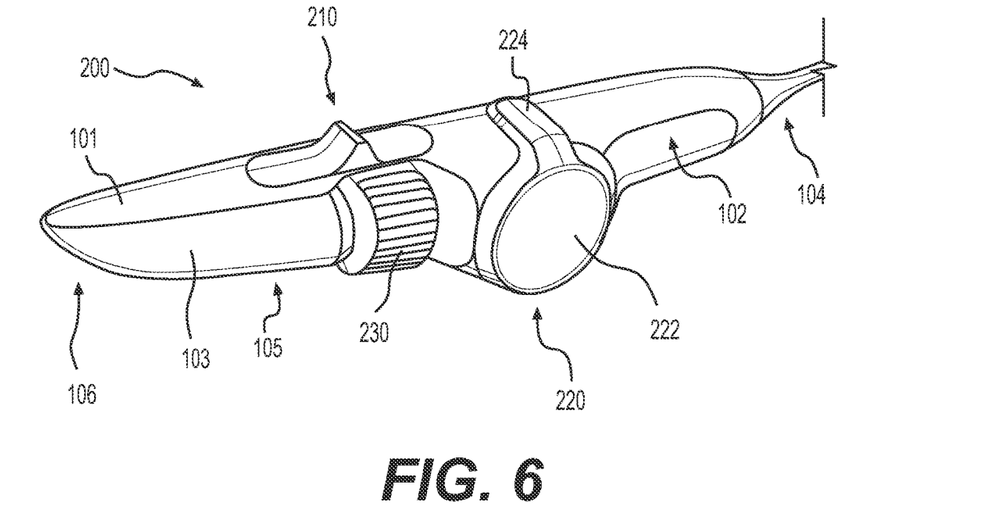
FIG. 6 is a partial perspective view of another exemplary medical device including a handle assembly, according to aspects of this disclosure.

Referring now to FIG. 6, another exemplary medical device 200 is schematically depicted in accordance with an example of this disclosure. Except as otherwise described below, the medical device 200 may be substantially similar to the medical device 100 described above, respectively, such that the same components are identified via the same reference numerals and/or similar components are identified via similar reference numerals plus the value of 100. Accordingly, it should be understood that the medical device 200 may be configured and operable like the medical device 100 except for the differences explicitly noted herein. For example, the medical device 200 may include the handle assembly 102, the shaft 108 (see FIG. 1), the articulation joint 140, and/or the end effector 146 (see FIG. 1).

As described above, the medical devices shown and described herein may include additional and/or fewer actuators positioned along various walls 101, 103, 105 (and/or surfaces) of the handle assembly 102. Further, the actuators of this disclosure may have various sizes, shapes, and/or configurations. For example, the medical device 200 includes one or more actuators 210, 220, 230 disposed along one or more walls 101, 103, 105 of the handle assembly 102, and that are configured to actuate one or more components of the medical device 200, such as, for example, an articulation joint 140 and/or an end effector 146. As described in detail above, the one or more actuators 210, 220, 230 may be disposed on the handle assembly 102 in an ergonomic manner to facilitate control of the medical device 200 with a single hand of a user.

In the example, the medical device 200 includes a first (actuation) actuator 210 positioned along the top wall 101 of the handle assembly 102, a second (articulation) actuator 220 positioned along at least a portion of the top wall 101 and at least one of the sidewalls 103 of the handle assembly 102, and a third (rotation) actuator 230 positioned along at least one of the sidewalls 103 of the handle assembly 102. In this instance, the second (articulation) actuator 220 and the third (rotation) actuator 230 may be positioned along the same sidewall 103 of the handle assembly 102, however, it should be understood that in other examples the second (articulation) actuator 220 and the third (rotation) actuator 230 may be positioned along opposing sidewalls 103 of the handle assembly (see FIG. 7).

Still referring to FIG. 6, the first (actuation) actuator 210 of the medical device 200 is configured to translate relative to the handle assembly 102, such as, for example, in one or more directions (e.g., distally, proximally, etc.) parallel to the central longitudinal axis 10 of the handle assembly 102. In the example, the first (actuation) actuator 210 is a button/actuator that is sized and shaped in the form of a slidable switch that extends outwardly from the top wall 101 of the handle assembly 102. The second (articulation) actuator 220 of the medical device 200 is configured to translate, pivot, and/or rotate relative to the handle assembly 102, such as, for example in one or more directions (e.g., distally, proximally, etc.) parallel to the central longitudinal axis 10 of the handle assembly 102.

For example, the second (articulation) actuator 220 may include a rocker 222 disposed along the sidewall 103 of the handle assembly 102 and a lever 224 disposed along the top wall 101 of the handle assembly 102. In the example, the rocker 222 and the lever 224 of the second (articulation) actuator 220 are integrally formed such that the rocker 222 and the lever 224 form a unitary structure. Accordingly, the rocker 222 of the second (articulation) actuator 220 is configured to rotate along the sidewall 103 about an axis (not shown) that is transverse (e.g., perpendicular) to the central longitudinal axis 10 of the handle assembly 102. Further, the lever 224 of the second (articulation) actuator 220 is configured to translate and/or pivot along the top wall 101 of the handle assembly 102. In the example, rocker 222 of the second (articulation) actuator 220 extends laterally outward from an exterior surface of the sidewall 103 of the handle assembly 102 and the lever 224 extends laterally outward from an exterior surface of the top wall 101 of the handle assembly 102.

Still referring to FIG. 6, the third (rotation) actuator 230 is configured to rotate (e.g., clockwise, counter-clockwise, etc.) along the sidewall 103 of the handle assembly 102 and about an axis (not shown) that is parallel to the central longitudinal axis 10 of the handle assembly 102. In the example, the third (rotation) actuator 230 is a button/actuator that is sized and shaped in the form of a roller. Further, the third (rotation) actuator 230 extends at least partially outward along the top wall 101 and the bottom wall 105 of the handle assembly 102 such that the third (rotation) actuator 230 is at least partially accessible along the top wall 101, the sidewall 103, and the bottom wall 105 of the handle assembly 102.

It should be understood that the actuators 210, 220, 230 of the medical device 200 are configured and operable identical to the actuators 110, 120, 130 of the medical device 100 shown and described above, respectively. Accordingly, the actuators 210, 220, 230 of the medical device 200 may actuate the articulation joint 140 and/or the end effector 146 of the medical device 200 in a substantially similar manner as the actuators 110, 120, 130 of the medical device 100 described in greater detail above. It should be appreciated that the medical device 200 may include additional and/or fewer actuators 210, 220, 230 on various other walls 101, 103, 105 (and/or surfaces) of the handle assembly 102 without departing from the scope of this disclosure. It should further be understood that, in other examples, the actuators 210, 220, 230 of the medical device 200 may have various other suitable configurations than those shown and described herein.

Figure 7:
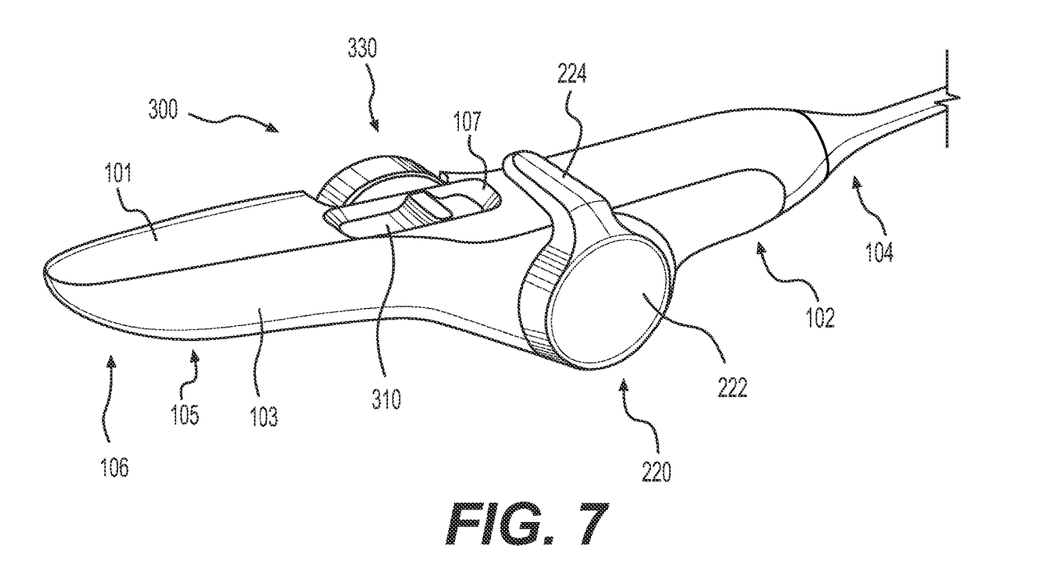
FIG. 7 is a partial perspective view of another exemplary medical device including a handle assembly, according to aspects of this disclosure.

Referring now to FIG. 7, another exemplary medical device 300 is schematically depicted in accordance with an example of this disclosure. Except as otherwise described below, the medical device 300 may be substantially similar to the medical device 100, 200 described above, respectively, such that the same components are identified via the same reference numerals and/or similar components are identified via similar reference numerals plus the value of 100. Accordingly, it should be understood that the medical device 300 may be configured and operable like the medical device 100, 200 except for the differences explicitly noted herein. For example, the medical device 300 may include the handle assembly 102, the shaft 108 (see FIG. 1), the articulation joint 140 (see FIG. 1), the end effector 146 (see FIG. 1), and/or the second (articulation) actuator 220.

In the example, the medical device 300 includes a first (actuation) actuator 310 positioned along the top wall 101 of the handle assembly 102 and a third (rotation) actuator 330 positioned along at least one of the sidewalls 103 of the handle assembly 102. In this instance, the second (articulation) actuator 220 and the third (rotation) actuator 330 may be positioned along opposing sidewalls 103 of the handle assembly 102. The first (actuation) actuator 310 of the medical device 300 is configured to translate relative to the handle assembly 102, such as, for example, in one or more directions (e.g., distally, proximally, etc.) parallel to the central longitudinal axis 10 of the handle assembly 102. In the example, the first (actuation) actuator 310 is a button that is sized and shaped in the form of a slidable switch that is disposed within a recess 107 formed along the top wall 101 of the handle assembly 102.

Still referring to FIG. 7, the third (rotation) actuator 330 is configured to rotate (e.g., clockwise, counter-clockwise, etc.) along the sidewall 103 of the handle assembly 102 and about an axis (not shown) that is transverse (e.g., perpendicular) to the central longitudinal axis 10 of the handle assembly 102. In the example, the third (rotation) actuator 330 is a button/actuator that is sized and shaped in the form of a roller. Further, the third (rotation) actuator 330 extends at least partially outward along at least the top wall 101 of the handle assembly 102 such that the third (rotation) actuator 330 is at least partially accessible along the top wall 101 and the sidewall 103 of the handle assembly 102.

It should be understood that the first (actuation) actuator 310 and the third (rotation) actuator 330 of the medical device 300 are configured and operable identical to the first (actuation) actuators 110, 210 and the third (rotation) actuators 130, 230 of the medical devices 100, 200 shown and described above, respectively. Accordingly, the actuators 310, 330 of the medical device 300 may actuate the articulation joint 140 and/or the end effector 146 of the medical device 300 in a substantially similar manner as the first (actuation) actuators 110, 210 and the third (rotation) actuators 130, 230 of the medical devices 100, 200 described in greater detail above. It should be appreciated that the medical device 300 may include additional and/or fewer actuators 310, 220, 330 on various other walls 101, 103, 105 (and/or surfaces) of the handle assembly 102 without departing from the scope of this disclosure. It should further be understood that, in other examples, the actuators 310, 220, 330 of the medical device 300 may have various other suitable configurations than those shown and described herein.

Figure 8:
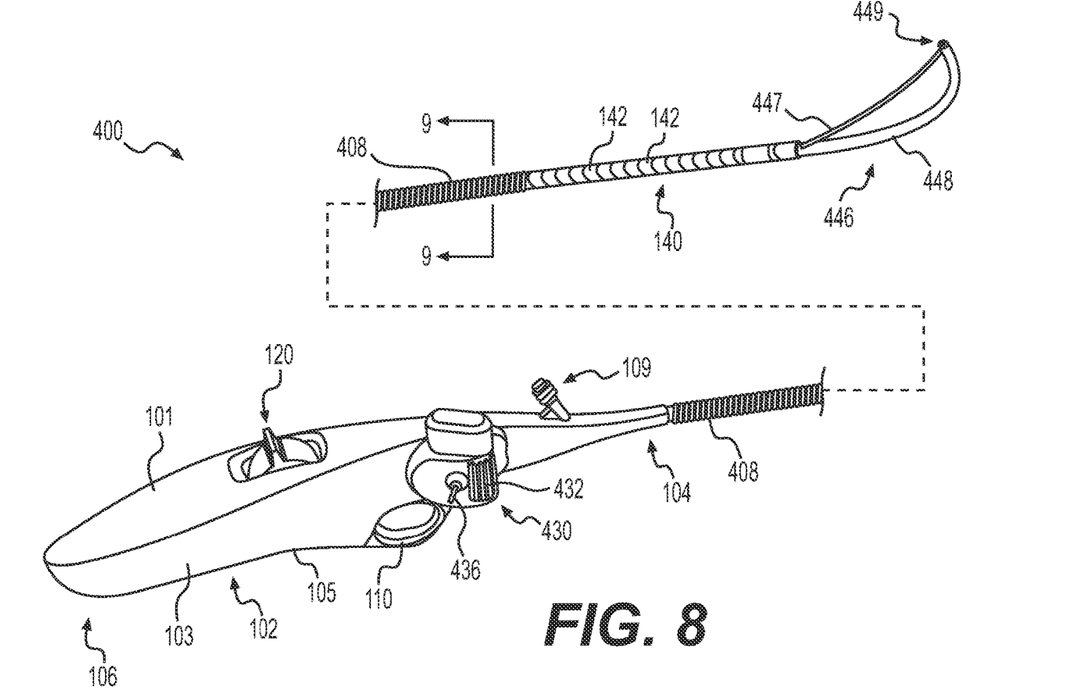
FIG. 8 is a perspective view of another exemplary medical device including a handle assembly and a coiled shaft, according to aspects of this disclosure.

Referring now to FIG. 8, another exemplary medical device 400 is schematically depicted in accordance with an example of this disclosure. Except as otherwise described below, the medical device 400 may be substantially similar to the medical device 100, 200, 300 described above, respectively, such that the same components are identified via the same reference numerals and/or similar components are identified via similar reference numerals plus the value of 100. Accordingly, it should be understood that the medical device 400 may be configured and operable like the medical device 100, 200, 300 except for the differences explicitly noted herein. For example, the medical device 400 may include the handle assembly 102 and the articulation joint 140.

The handle assembly 102 of the medical device 400 includes the first (actuation) actuator 110, the second (articulation) actuator 120, and a third (guidewire) actuator 430. The third (guidewire) actuator 430 is positioned along at least one of the sidewalls 103 of the handle assembly 102. The third (guidewire) actuator 430 includes one or more rollers 432 configured to rotate about an axis that is transverse to the central longitudinal axis 10 of the handle assembly 102 (see FIG. 1). As described further herein, the third (guidewire) actuator 430 is configured and operable to actuate one or more components of the medical device 400, such as, for example, a guidewire 436. In the example, the handle assembly 102 further includes an irrigation port 109 disposed along the top wall 101 that is in fluid communication with one or more lumens of the handle assembly 102 and/or one or more other components of the medical device 400 (e.g., a working channel of a shaft 408).

Still referring to FIG. 8, the medical device 400 may include a coiled shaft 408 extending distally from the distal end 104 of the handle assembly 102, with the articulation joint 140 positioned at a distal end of the coiled shaft 408. Further, the medical device 400 may include an end effector 446 positioned at a distal end of the articulation joint 140. The end effector 446 of the medical device 400 may extends distally from the distalmost articulation link 142 of the articulation joint 140. Further, the end effector 446 may include an extension line 447, a tubular member 448, and a distal opening 449. In the example, the extension line 447 and the tubular member 448 may include a nonlinear (e.g., curved) configuration such that the distal opening 449 of the end effector 446 is positioned at least partially transverse to a proximal end of the end effector 446.

Figure 9:
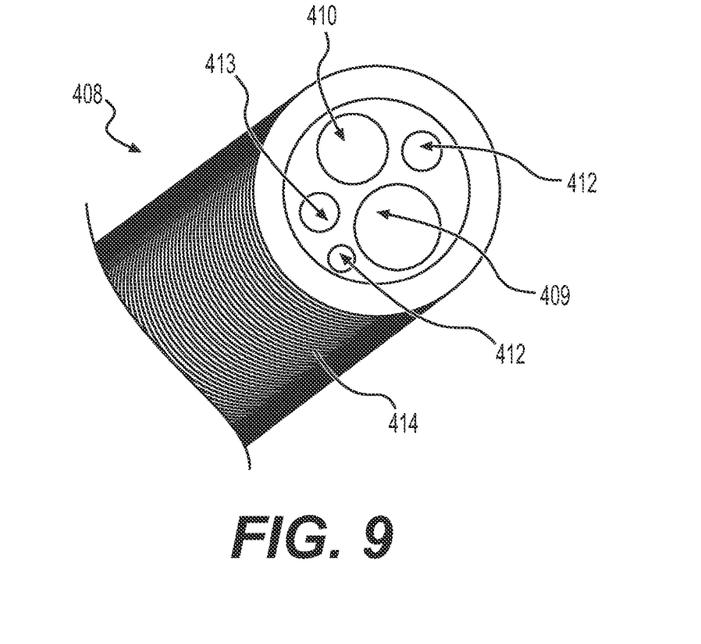
FIG. 9 is a cross-sectional perspective view of the coiled shaft of FIG. 8, according to aspects of this disclosure.

The tubular member 448 of the end effector 446 may include one or more inner lumens that are aligned with and/or in communication with one or more working channels of the coiled shaft 408 (see FIG. 9). Further, the distal opening 449 at a distal end of the tubular member 448 may be further aligned with and/or in communication with the one or more working channels of the coiled shaft 408 via the one or more inner lumens of the tubular member 448. The tubular member 448 is configured and operable to position one or more medical devices and/or instruments received through the handle assembly 102 and/or coiled shaft 408 proximate to a target treatment site. The extension line 447 of the end effector 446 is secured to, and between, a proximal end of the tubular member 448 and a distal end of the tubular member 448, adjacent to the distal opening 449.

Still referring to FIG. 8, the extension line 447 is configured to tension a distal end of the tubular member 448 toward the proximal end of the tubular member 448 to form the nonlinear configuration of the tubular member 448. In other words, the extension line 447 is operable to apply a force on a distal end of the tubular member 448 to thereby form a bend and/or angle along a longitudinal length of the tubular member 448 between the opposing terminal ends of the tubular member 448. In this instance, the distal opening 449 at a distal end of the tubular member 448 is positioned and/or aligned relatively transverse to the central longitudinal axis 10 of the handle assembly 102 (see FIG. 1), rather than collinear with and/or parallel to the central longitudinal axis 10. It should be appreciated that with the tubular member 448 of the end effector 446 including the nonlinear and/or curved configuration, the medical device 400 may facilitate positioning one or more medical instruments and/or devices (e.g., devices/guidewire 436 received through the coiled shaft 408) at a target treatment site.

Referring now to FIG. 9, the coiled shaft 408 may include one or more lumens extending therethrough, such as, for example, one or more working channels that are sized and shaped to receive one or more medical instruments and/or devices therethrough. By way of example only, the coiled shaft 408 of the medical device 400 may include a working channel 409 configured to receive a guidewire (e.g., guidewire 436), a working channel 410 configured to receive an imaging device (e.g., camera), a pair of working channels 412 configured to receive the pair of drive wires 122B, 122T, and/or a working channel 413 configured to receive a cautery wire. It should be understood that the number and arrangement of working channels 409, 410, 412, 413 shown and described herein are merely illustrative such that the coiled shaft 408 may include additional, fewer, and/or various other lumens/working channels configurations.

The coiled shaft 408 of the medical device 400 may further include an exterior surface having a protective plastic sheath 414 disposed thereon. In the example, the one or more working channels 409, 410, 412, 413 of the coiled shaft 408 are insulated by the protective plastic sheath 414 included along the exterior of the coiled shaft 408. In some examples, the coiled shaft 408 may be a coil disposed over the working channels 409, 410, 412, 413. For example, the coiled shaft 408 may be a coil having a pair of layers (e.g., a dual-layer coil), with a first layer extending about the working channels 409, 410, 412, 413 in a first direction (e.g., clockwise) and a second layer extending about the working channels 409, 410, 412, 413 in a second direction (e.g., counter-clockwise).

Figure 10:
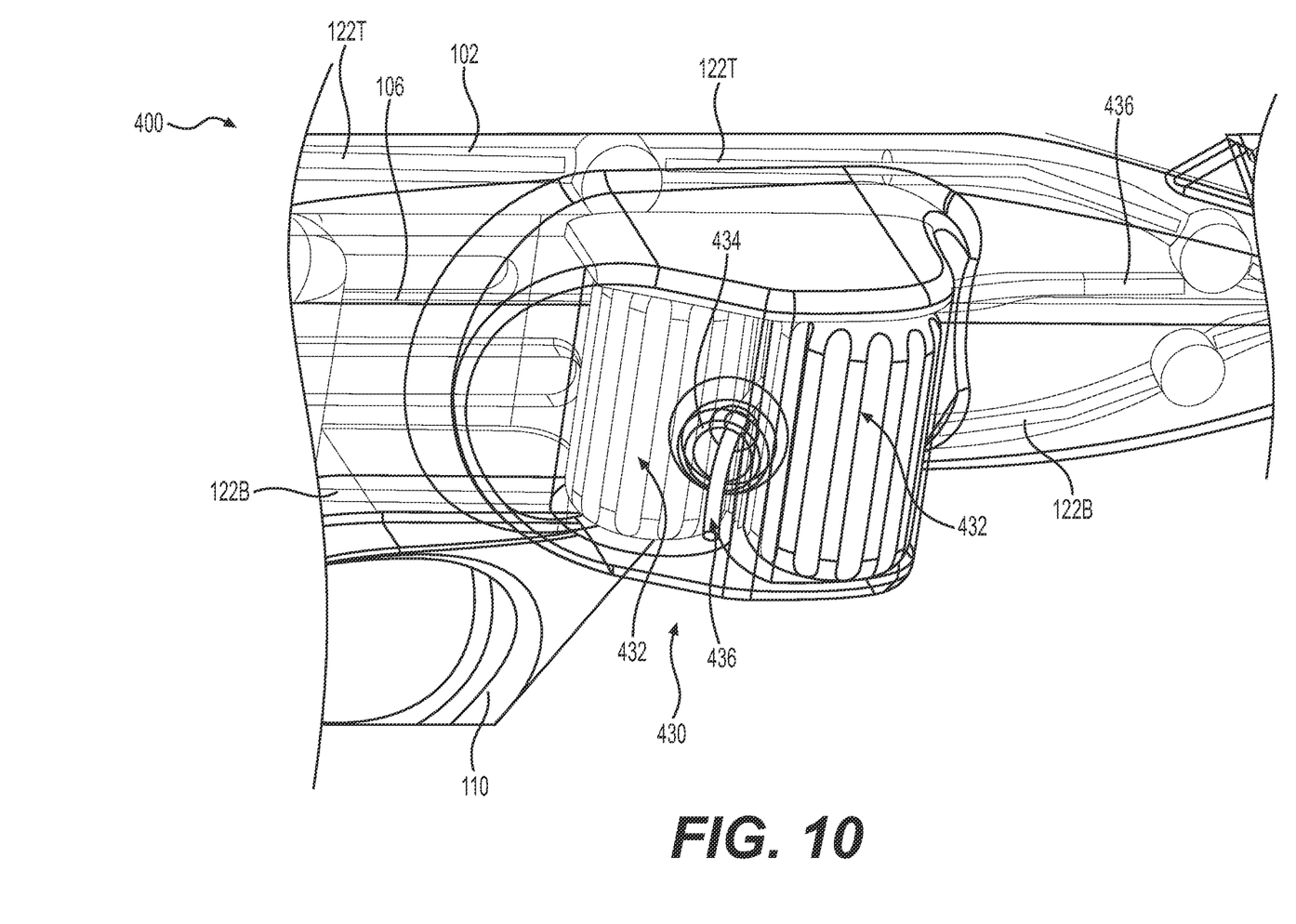
FIG. 10 is a partial perspective view of the handle assembly of FIG. 8 including an actuator with a guidewire disposed therein.

Referring now to FIG. 10, a partial schematic of the handle assembly 102 of the medical device 400 is depicted. In the example, the third (guidewire) actuator 430 may include a pair of rollers 432 disposed within the handle assembly 102, with at least one of the pair of rollers 432 being accessible to a user of the medical device 400 (e.g. extending through a surface of the handle assembly 102). The pair of rollers 432 of the third (guidewire) actuator 430 are configured to rotate about an axis that is at least partially transverse (e.g., perpendicular) to the central longitudinal axis 10 of the handle assembly 102 (see FIG. 1). The handle assembly 102 of the medical device 400 may further include an opening 434 along the third (guidewire) actuator 430 that is sized, shaped and configured to receive a guidewire 436 therethrough.

The opening 434 of the handle assembly 102 is positioned in alignment with a region between the pair of rollers 432 of the third (guidewire) actuator 430. In this instance, the guidewire 436 inserted through the opening 434 is received between the pair of rollers 432. Accordingly, it should be appreciated that actuation (e.g., rotation) of the third (guidewire) actuator 430 in a first direction (e.g., clockwise, counter-clockwise, etc.) may provide for a relative movement of the guidewire 436 in the handle assembly 102 and/or the coiled shaft 408 in a first direction, and actuation of the third (guidewire) actuator 430 in a second direction may provide for another relative movement of the guidewire 436 in the handle assembly 102 and/or the coiled shaft 408.

Still referring to FIG. 10, in the example, the pair of rollers 432 of the third (guidewire) actuator 430 may each include one or more ridges and/or cavities (formed between an adjacent pair of ridges) extending along a longitudinal length of the roller 432. The one or more ridges and/or cavities of the pair of rollers 432 may be configured and operable to engage the guidewire 436 to facilitate movement of the guidewire 436 relative to the handle assembly 102. Although not shown, it should be understood that a proximal end of the guidewire 436 may be positioned proximate to the opening 434 of the handle assembly 102 and a distal end of the guidewire 436 may extend through the working lumen 409 of the coiled shaft 408 and distally from the distal opening 449 of the end effector 436.

Each of the aforementioned devices, assemblies, and methods may be used to facilitate access to a target treatment site and provide enhanced control of ancillary tools/devices for use at the target treatment site. By providing a medical device with a handle assembly capable of controlling and moving a plurality of tools/devices (end effector) coupled to the medical device, a user may interact with a target treatment site using the various tools/devices of the medical instrument during a procedure via an intuitive interface of the handle assembly. In this instance, a user may reduce overall procedure time, increase efficiency of procedures, and/or avoid unnecessary harm to a subject's body caused by limited control of the ancillary tools/devices. Additionally, a user may control and move the plurality of tools/devices (end effector) of the medical device with a single hand, and about a plurality of degrees of freedom, pursuant to the intuitive interface of the handle assembly.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
a handle including a plurality of actuators;
a shaft extending from the handle, wherein the shaft defines a central longitudinal axis extending through the shaft; and
an end effector at a distal end of the shaft;
wherein a first actuator of the plurality of actuators is configured to actuate the end effector in response to translation of the first actuator relative to the handle along an axis parallel to the central longitudinal axis;
wherein a second actuator of the plurality of actuators is configured to deflect the end effector relative to the shaft in response to pivoting the second actuator about an axis transverse to the central longitudinal axis; and
wherein a third actuator of the plurality of actuators is configured to rotate the end effector relative to the shaft in response to rotation of the third actuator relative to the handle about the central longitudinal axis.

2. The medical device of claim 1, wherein the first actuator of the plurality of actuators includes a trigger positioned along a bottom wall of the handle.

3. The medical device of claim 2, wherein the trigger is configured to translate proximally and distally along the bottom wall of the handle and along the axis parallel to the central longitudinal axis of the shaft.

4. The medical device of claim 2, further comprising an actuation wire coupled to and extending between the trigger and the end effector.

5. The medical device of claim 4, wherein at least a portion of the trigger is movably received within an inner slot of the handle and is coupled to the actuation wire.

6. The medical device of claim 5, wherein actuating the trigger moves the trigger along the inner slot and the actuation wire along the shaft to actuate the end effector.

7. The medical device of claim 1, wherein the second actuator of the plurality of actuators includes a rocker with a protrusion positioned along a top wall of the handle.

8. The medical device of claim 7, further comprising a pair of drive wires coupled to and extending between the rocker and the distal end of the shaft, wherein a first drive wire of the pair of drive wires extends along a first side of the third actuator, wherein a second drive wire of the pair of drive wires extends along a second side of the third actuator, and wherein the second side is opposite to the first side.

9. The medical device of claim 8, wherein actuating the rocker moves at least one of the pair of drive wires along the shaft to deflect the distal end of the shaft.

10. The medical device of claim 1, wherein the third actuator of the plurality of actuators includes a roller positioned along a sidewall of the handle.

11. The medical device of claim 1, wherein the handle includes one or more walls defining an exterior of the handle, wherein each of the first actuator, the second actuator, and the third actuator are positioned along different walls of the one or more walls of the handle.

12. The medical device of claim 11, further comprising an actuation wire coupled to and extending between the third actuator and the end effector, wherein actuating the third actuator rotates the actuation wire and the end effector relative to the shaft.

13. A medical device comprising:
a shaft including a distal end and a proximal end;
an end effector at the distal end of the shaft; and
a handle at the proximal end of the shaft, wherein the handle includes:
  a first actuator that is movable in a first direction relative to the handle, wherein the first actuator is configured to actuate an actuator wire coupled to the end effector, wherein the end effector is actuated in response to moving the first actuator in the first direction;
  a second actuator that is movable in a second direction relative to the handle, wherein, in response to moving the second actuator in the second direction, the second actuator is configured translate a first drive wire and a second drive wire longitudinally to deflect the end effector relative to the shaft; and
  a third actuator that is movable in a third direction relative to the handle, wherein the third actuator is configured to rotate the actuator wire coupled to the end effector, wherein the end effector is rotated relative to the shaft in response to moving the third actuator in the third direction;
wherein the first direction is parallel to a longitudinal axis of the shaft, and the third direction is about the longitudinal axis of the handle,
wherein the first drive wire extends around the third actuator on a first side of the handle, wherein the second drive wire extends around the third actuator on a second side of the handle, and wherein the second side of the handle is opposite the first side of the handle.

14. The medical device of claim 1, wherein at least a portion of the first actuator is distal to the second actuator and proximal of the third actuator.

15. The medical device of claim 1, further comprising an actuation wire, wherein a first portion of the actuation wire is movably coupled to the first actuator, wherein a second portion of the actuation wire is fixedly coupled to a rotation joint, wherein the rotation joint is rotatably fixed relative to the third actuator and translatable relative to the third actuator.

* * * * *